(12) United States Patent
Keller

(10) Patent No.: US 10,595,926 B2
(45) Date of Patent: *Mar. 24, 2020

(54) ENERGY-BASED MEDICAL DEVICES

(71) Applicant: COVIDIEN LP, Mansfield, MA (US)

(72) Inventor: Craig A. Keller, Boulder, CO (US)

(73) Assignee: Covidien LP, Mansfield, MA (US)

(*) Notice: Subject to any disclaimer, the term of this patent is extended or adjusted under 35 U.S.C. 154(b) by 333 days.

This patent is subject to a terminal disclaimer.

(21) Appl. No.: 15/623,447

(22) Filed: Jun. 15, 2017

(65) Prior Publication Data

US 2017/0281257 A1 Oct. 5, 2017

Related U.S. Application Data

(63) Continuation of application No. 14/029,909, filed on Sep. 18, 2013, now Pat. No. 9,687,290.

(60) Provisional application No. 61/708,833, filed on Oct. 2, 2012.

(51) Int. Cl.
| | |
|---|---|
| *A61B 18/12* | (2006.01) |
| *A61B 18/08* | (2006.01) |
| *A61B 18/14* | (2006.01) |
| *A61B 18/00* | (2006.01) |

(52) U.S. Cl.
CPC ........ *A61B 18/1206* (2013.01); *A61B 18/085* (2013.01); *A61B 18/1445* (2013.01); *A61B 2018/0063* (2013.01); *A61B 2018/00095* (2013.01); *A61B 2018/00101* (2013.01); *A61B 2018/00642* (2013.01); *A61B 2018/00791* (2013.01); *A61B 2018/1226* (2013.01); *A61B 2018/1495* (2013.01)

(58) Field of Classification Search
CPC ... A61B 18/085; A61B 18/10; A61B 18/1445; A61B 2018/00095; A61B 2018/00101; A61B 2018/0063; A61B 2018/00642; A61B 2018/00791; A61B 2018/1226; A61B 2018/1495

See application file for complete search history.

(56) References Cited

U.S. PATENT DOCUMENTS

| | | |
|---|---|---|
| 3,878,619 A | 4/1975 | Hodgett et al. |
| 3,944,904 A | 3/1976 | Hase |
| D249,549 S | 9/1978 | Pike |
| D263,020 S | 2/1982 | Rau, III |

(Continued)

FOREIGN PATENT DOCUMENTS

| | | |
|---|---|---|
| CN | 201299462 Y | 9/2009 |
| DE | 2415263 A1 | 10/1975 |

(Continued)

OTHER PUBLICATIONS

U.S. Appl. No. 12/336,970, filed Dec. 17, 2008, Paul R. Sremeich.

(Continued)

*Primary Examiner* — Daniel W Fowler
(74) *Attorney, Agent, or Firm* — Carter, DeLuca & Farrell, LLP

(57) ABSTRACT

A medical device includes an energy-generating unit configured to produce energy for conduction through tissue to treat tissue. Waste heat produced by the energy-generating unit during energy production is conducted to tissue to facilitate treating tissue.

14 Claims, 3 Drawing Sheets

(56) References Cited

U.S. PATENT DOCUMENTS

| | | |
|---|---|---|
| 4,662,433 A | 5/1987 | Cahn et al. |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,164,884 A | 11/1992 | Pesola |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,415,655 A | 5/1995 | Fuller et al. |
| 5,449,531 A | 9/1995 | Zhu et al. |
| D384,413 S | 9/1997 | Zlock et al. |
| 5,676,692 A | 10/1997 | Sanghvi et al. |
| 5,726,605 A | 3/1998 | Morse et al. |
| 5,744,920 A | 4/1998 | Orton |
| H001745 H | 8/1998 | Paraschac |
| 5,827,281 A | 10/1998 | Levin |
| D402,028 S | 12/1998 | Grimm et al. |
| D408,018 S | 4/1999 | McNaughton |
| D416,089 S | 11/1999 | Barton et al. |
| 5,980,518 A | 11/1999 | Carr et al. |
| D424,694 S | 5/2000 | Tetzlaff et al. |
| D425,201 S | 5/2000 | Tetzlaff et al. |
| H001904 H | 10/2000 | Yates et al. |
| 6,216,704 B1 | 4/2001 | Ingle |
| 6,249,706 B1 | 6/2001 | Sobota et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H002037 H | 7/2002 | Yates et al. |
| D465,281 S | 11/2002 | Lang |
| D466,209 S | 11/2002 | Bon |
| D493,888 S | 8/2004 | Reschke |
| 6,770,072 B1 * | 8/2004 | Truckai ............. A61B 18/1445 606/45 |
| D496,997 S | 10/2004 | Dycus et al. |
| D499,181 S | 11/2004 | Dycus et al. |
| D502,994 S | 3/2005 | Blake, III |
| 6,908,463 B2 | 6/2005 | Treat et al. |
| 6,926,716 B2 | 8/2005 | Baker et al. |
| 6,929,644 B2 | 8/2005 | Truckai et al. |
| D509,297 S | 9/2005 | Wells |
| 6,994,709 B2 | 2/2006 | Iida |
| 7,025,763 B2 | 4/2006 | Karasawa et al. |
| D525,361 S | 7/2006 | Hushka |
| 7,108,694 B2 | 9/2006 | Miura et al. |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,326,202 B2 | 2/2008 | McGaffigan |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,128,624 B2 | 3/2012 | Couture et al. |
| 8,142,425 B2 | 3/2012 | Eggers |
| D661,394 S | 6/2012 | Romero et al. |
| 8,197,472 B2 | 6/2012 | Lau et al. |
| 8,679,140 B2 | 3/2014 | Butcher |
| RE44,834 E | 4/2014 | Dumbauld et al. |
| 8,968,311 B2 | 3/2015 | Allen, IV et al. |
| 2003/0078578 A1 * | 4/2003 | Truckai ............. A61B 18/1442 606/51 |
| 2003/0139742 A1 | 7/2003 | Wampler et al. |
| 2003/0143958 A1 | 7/2003 | Elias et al. |
| 2003/0236518 A1 | 12/2003 | Marchitto et al. |
| 2004/0078035 A1 | 4/2004 | Kanehira et al. |
| 2004/0087943 A1 | 5/2004 | Dycus et al. |
| 2005/0048720 A1 | 3/2005 | Graham et al. |
| 2005/0143790 A1 | 6/2005 | Kipke et al. |
| 2005/0203497 A1 | 9/2005 | Speeg et al. |
| 2005/0240151 A1 | 10/2005 | Hansmann et al. |
| 2006/0052779 A1 * | 3/2006 | Hammill ............ A61B 18/1442 606/51 |
| 2006/0195079 A1 * | 8/2006 | Eberl ................. A61B 18/1442 606/41 |
| 2007/0215329 A1 | 9/2007 | Schwab |
| 2008/0119870 A1 | 5/2008 | Williams |
| 2008/0268333 A1 | 10/2008 | Barrella et al. |
| 2010/0063422 A1 | 3/2010 | Hynynen et al. |
| 2010/0185197 A1 | 7/2010 | Sakao et al. |
| 2013/0053839 A1 | 2/2013 | Hotto et al. |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |

(56) References Cited

FOREIGN PATENT DOCUMENTS

| | | |
|---|---|---|
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 0010000195 A | 1/1995 |
| JP | 07265328 A | 10/1995 |
| JP | H08-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 09000538 A | 1/1997 |
| JP | H0910223 A | 1/1997 |
| JP | 9-122138 A | 5/1997 |
| JP | H10-24051 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175502 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 01546041 A1 | 8/2001 |
| WO | 02/45589 A2 | 6/2002 |
| WO | 2006021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/868,732, filed Apr. 23, 2013, Mueller.
U.S. Appl. No. 13/893,527, filed May 14, 2013, Homer.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 14, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.

(56) References Cited

OTHER PUBLICATIONS

Johnson et al. "Evaluation of the LigaSure Vessel Sealing System in Hemorrhoidectormy" American College of Surgeons (ACS) Clinicla Congress Poster (2000).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: a Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Palazzo et al. "Randomized clinical trial of Ligasure versus open haemorrhoidectomy" British Journal of Surgery 2002, 39, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Michael Choti, "Abdominoperineal Resection with the LigaSure Vessel Sealing System and LigaSure Atlas 20 cm Open Instrument"; Innovations That Work, Jun.2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Muller et al., "Extended Left Hemicolectomy Using the LigaSure Vessel Sealing System" Innovations That Work, Sep. 1999.
Carus et al., "Initial Experience With the LigaSure Vessel Sealing System in Abdominal Surgery" Innovations That/Work, Jun. 2002.
Heniford et al. "Initial Research and Clinical Results with an Electrothermal Bipolar Vessel Sealer" Oct. 1999.
W. Scott Helton, "LigaSure Vessel Sealing System: Revolutionary Hemostasis Product for General Surgery"; Sales/Product Literature 1999.
Olsson et al. "Radical Cystectomy in Females" Current Surgical Techniques in Urology, vol. 14, Issue 3, 2001.
Sayfan et al. "Sutureless Closed Hemorrhoidectomy: A New Technique" Annals of Surgery vol. 234 No. 1 Jul. 2001; pp. 21-24.
Craig Johnson, "Use of the LigaSure Vessel Sealing System in Bloodless Hemorrhoidectomy" Innovations That Work, Mar. 2000.
Jarrett et al., "Use of the LigaSure Vessel Sealing System for Peri-Hilar Vessels in Laparoscopic Nephrectomy" Sales/Product Literature 2000.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.

* cited by examiner

ENERGY-BASED MEDICAL DEVICES

CROSS REFERENCE TO RELATED APPLICATION

The present application is a continuation application of U.S. patent application Ser. No. 14/029,909, filed on Sep. 18, 2013, now U.S. Pat. No. 9,687,290, which claims the benefit of and priority to U.S. Patent Application No. 61/708,833, filed on Oct. 2, 2012, the entire contents of which each of which are incorporated herein by reference.

BACKGROUND

Technical Field

The present disclosure relates to medical devices and, more particularly, to medical devices capable of heating tissue to treat tissue.

Background of Related Art

Energy-based medical devices are typically used in conjunction with surgical generators (external generators or portable generators incorporated into the instruments themselves) to apply and control the application of energy to tissue to treat tissue. Electrosurgical forceps, for example, include one or more electrodes incorporated into jaw members and coupled to a generator that are used to grasp and apply energy to tissue. More specifically, these electrosurgical systems, e.g., the forceps and associated generator, utilize both the mechanical clamping action of the jaw members and the electrical energy provided by the generator and delivered to tissue via the electrode(s) to treat tissue.

These and other similar surgical systems typically include separate power, control, and energy generation components that work in cooperation with one another to achieve the desired tissue effect. However, each of these components produces waste heat which needs to be dissipated, thereby increasing the complexity of the system and reducing the efficiency of the system.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any of the other aspects described herein.

In accordance with the present disclosure, a medical device is provided including an energy-generating unit configured to produce energy for conduction through tissue to treat tissue. Waste heat produced by the energy-generating unit during energy production is also conducted to tissue to facilitate treating tissue.

In aspects, the medical device further includes a conductive tissue treating surface configured to connect to the energy-generating unit for conducting energy though tissue to treat tissue.

In aspects, the tissue treating surface is thermally coupled to the energy-generating unit such that the waste heat produced by the energy-generating unit is conducted to the tissue treating surface to facilitate treating tissue.

In aspects, the energy-generating unit includes one or more integrated circuits. The integrated circuit(s) may be part of a plurality of integrated circuits formed as a multi-chip-module on a substrate.

In aspects, the integrated circuit(s) is disposed on a printed circuit board substrate.

In aspects, the medical device further includes a control unit configured to control the energy-generating unit. Waste heat produced by the control unit in controlling the energy-generating unit may be conducted to tissue to facilitate treating tissue.

In aspects, the medical device further includes a power source operably coupled to the energy-generating unit. Waste heat produced by the power source may be conducted to tissue to facilitate treating tissue.

A medical device provided in accordance with the present disclosure includes an energy-generating unit configured to produce energy and conduct energy through tissue to treat tissue, and a control unit configured to control the energy-generating unit. Waste heat produced by the control unit is conducted to tissue to facilitate treating tissue.

In aspects, the medical device further includes a conductive tissue treating surface configured to connect to the energy-generating unit for conducting energy though tissue to treat tissue.

In aspects, the tissue treating surface is thermally coupled to the control unit such that the waste heat produced by the control unit is conducted to the tissue treating surface to facilitate treating tissue.

In aspects, the control unit is disposed on a substrate.

In aspects, wherein waste heat produced by the energy-generating unit is conducted to tissue to facilitate treating tissue.

In aspects, a power source is operably coupled to the energy-generating unit. Waste heat produced by the power source is conducted to tissue to facilitate treating tissue.

Provided in accordance with the present disclosure is a medical device including an energy-generating unit configured to produce energy, a power source configured to supply power to the energy-generating unit, a control unit configured to control the energy-generating unit, and a conductive tissue treating surface coupled to the energy-generating unit and configured to conduct energy produced by the energy-generating unit through tissue to treat tissue. Waste heat produced by the energy-generating unit, the power source, and/or the control unit is conducted to tissue via the tissue treating surface to facilitate treating tissue.

BRIEF DESCRIPTION OF THE DRAWINGS

Various aspects of the present disclosure are described herein with reference to the drawings wherein like reference numerals identify similar or identical elements:

FIG. 4 is a front, perspective view of a surgical tissue clip configured for use in accordance with the present disclosure;

DETAILED DESCRIPTION

There are a wide variety of medical devices that effect the heating of tissue to treat tissue. Tissue heating can be accomplished by Joule heating, e.g., passing current through tissue; conductive heating, e.g., placing a heated surface in contact with or in close proximity to tissue; dielectric heating, e.g., applying a changing electric field to tissue; and/or frictional heating, e.g., creating friction within tissue. Various systems, e.g., power systems, energy generating systems, and/or control systems, are used to supply energy to tissue to heat tissue and to control the heating of tissue. The present disclosure provides for the use of the waste heat produced by these systems to facilitate the heating of tissue.

Figure 1:
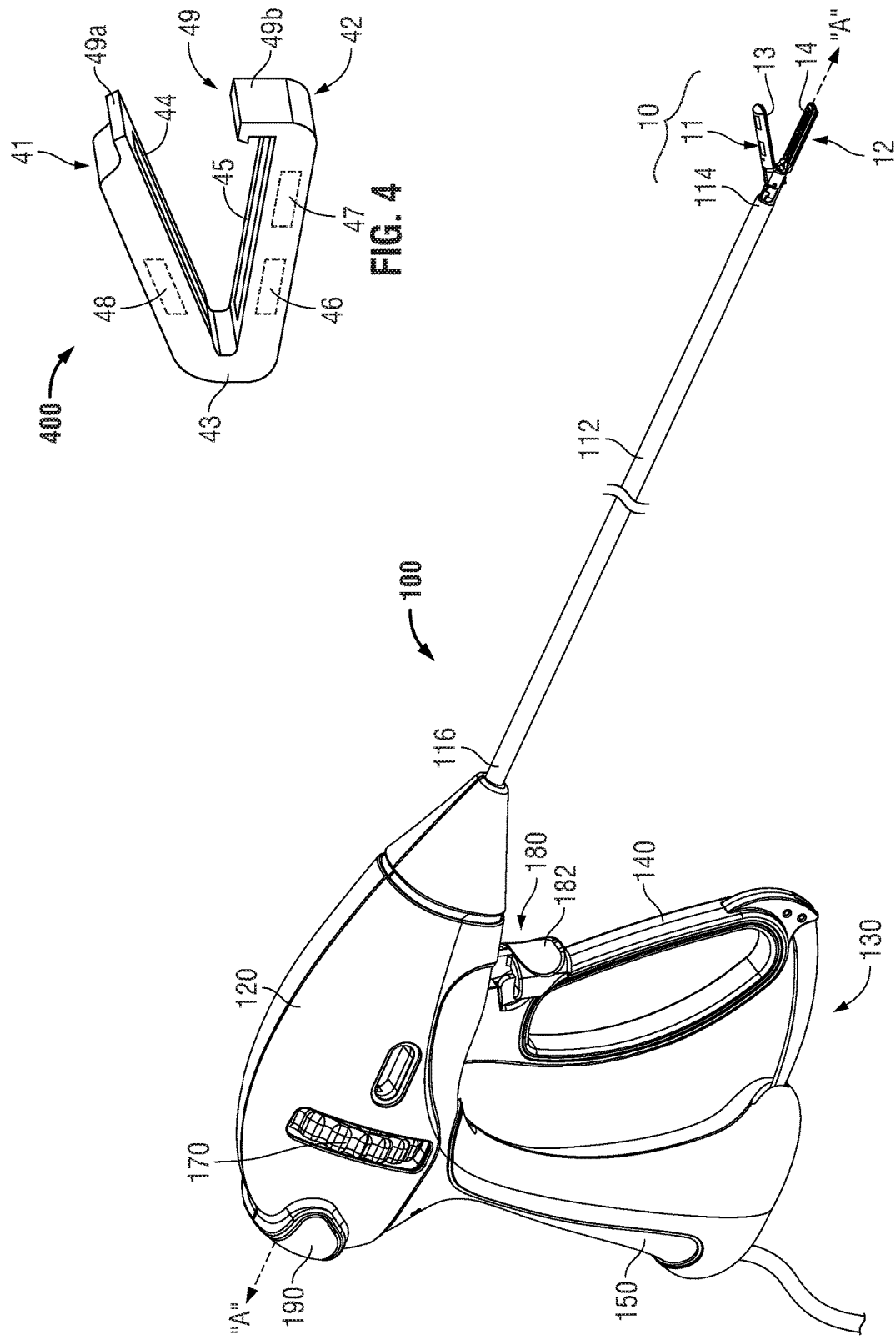
FIG. 1 is a front, perspective view of an endoscopic surgical forceps configured for use in accordance with the present disclosure.
Figure 2:
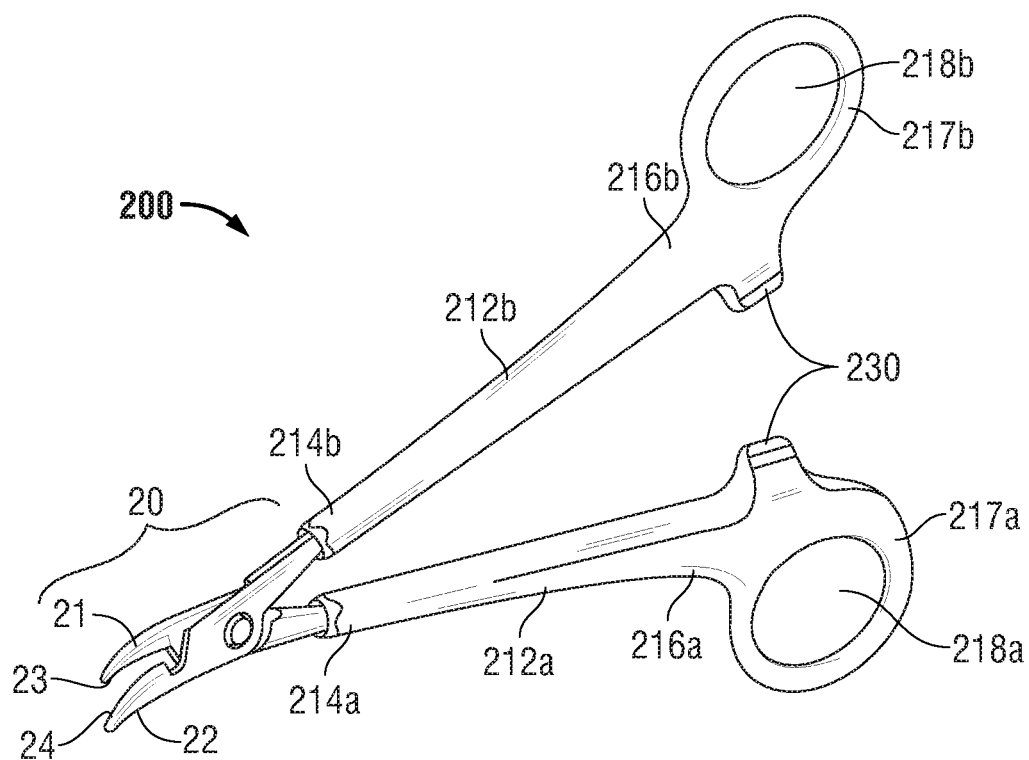
FIG. 2 is a front, perspective view of an open surgical forceps configured for use in accordance with the present disclosure.
Figure 3:
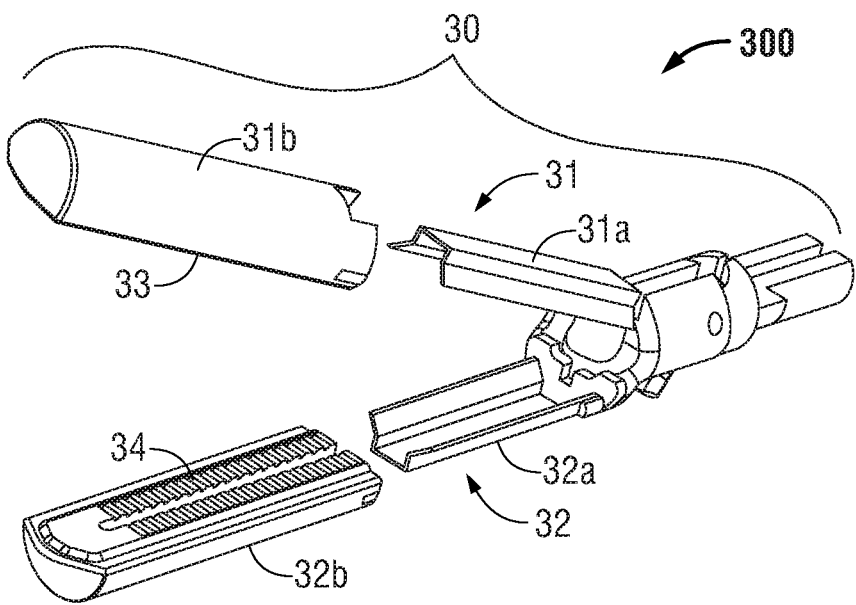
FIG. 3 is a front, perspective view of the distal end of a surgical forceps including reposable jaw members configured for use in accordance with the present disclosure.

Referring now to FIGS. 1-4, FIG. 1 depicts an endoscopic surgical forceps 100 for use in connection with endoscopic surgical procedures; FIG. 2 depicts an open surgical forceps 200 contemplated for use in connection with traditional open surgical procedures; FIG. 3 depicts a reposable forceps 300; and FIG. 4 depicts a tissue clip 400. For the purposes herein, either endoscopic forceps 100, open forceps 200, reposable forceps 300, tissue clip 400, or any other suitable surgical instrument may be utilized in accordance with the present disclosure. Obviously, different electrical and mechanical connections and considerations apply to each particular type of instrument; however, the novel aspects with respect to the end effector assembly and its operating characteristics remain generally consistent regardless of the configuration of the instrument used therewith.

Turning now to FIG. 1, endoscopic forceps 100 defines a longitudinal axis "A-A" and includes a housing 120, a handle assembly 130, a rotating assembly 170, a trigger assembly 180 and an end effector assembly 10. Forceps 100 further includes a shaft 112 having a distal end 114 configured to mechanically engage end effector assembly 10 and a proximal end 116 that mechanically engages housing 120. Forceps 100 may further include a surgical cable extending therefrom and configured to connect forceps 100 to a power source (not shown), or may alternatively be configured as a battery powered instrument having an internal or integrated power source (not shown). The power source (not shown), as will be described in greater detail below, provides power to end effector assembly 10 such that at least one of the jaw members 11 and 12 of end effector assembly 10 may be energized to treat tissue grasped therebetween, e.g., upon activation of activation switch 190.

With continued reference to FIG. 1, handle assembly 130 includes fixed handle 150 and a movable handle 140. Fixed handle 150 is integrally associated with housing 120 and handle 140 is movable relative to fixed handle 150. Rotating assembly 170 is rotatable in either direction about a longitudinal axis "A-A" to rotate end effector 10 about longitudinal axis "A-A." Housing 120 houses the internal working components of forceps 100.

End effector assembly 10 is shown attached at distal end 114 of shaft 112 and includes a pair of opposing jaw members 11 and 12. Each of jaw members 11 and 12 includes an electrically-conductive tissue treating surface 13, 14, respectively. End effector assembly 10 is designed as a unilateral assembly, i.e., where jaw member 12 is fixed relative to shaft 112 and jaw member 11 is movable relative to shaft 112 and fixed jaw member 12. However, end effector assembly 10 may alternatively be configured as a bilateral assembly, i.e., where both jaw member 11 and jaw member 12 are movable relative to one another and to shaft 112. In some embodiments, a knife assembly (not shown) is disposed within shaft 112 and a knife channel 615, 625 (FIG. 6) is defined within one or both jaw members 11, 12 to permit reciprocation of a knife blade (not shown) therethrough, e.g., upon activation of trigger 182 of trigger assembly 180. The particular features of end effector assembly 10 will be described in greater detail hereinbelow.

Continuing with reference to FIG. 1, movable handle 140 of handle assembly 130 is ultimately connected to a drive assembly (not shown) that, together, mechanically cooperate to impart movement of jaw members 11 and 12 between a spaced-apart position and an approximated position to grasp tissue between tissue treating surfaces 13 and 14 of jaw members 11, 12, respectively. As shown in FIG. 1, movable handle 140 is initially spaced-apart from fixed handle 150 and, correspondingly, jaw members 11, 12 are in the spaced-apart position. Movable handle 140 is depressible from this initial position to a depressed position corresponding to the approximated position of jaw members 11, 12.

Referring now to FIG. 2, open forceps 200 is shown including two elongated shafts 212a and 212b, each having a proximal end 216a and 216b, and a distal end 214a and 214b, respectively. Forceps 200 is configured for use with an end effector assembly 20 that is similar to end effector assembly 10 of forceps 100 (see FIG. 1). More specifically, end effector assembly 20 is attached to distal ends 214a and 214b of shafts 212a and 212b, respectively and includes a pair of opposing jaw members 21 and 22 that are movable relative to one another. Each shaft 212a and 212b includes a handle 217a and 217b disposed at the proximal end 216a and 216b thereof. Each handle 217a and 217b defines a finger hole 218a and 218b therethrough for receiving a finger of the user. As can be appreciated, finger holes 218a and 218b facilitate movement of shafts 212a and 212b relative to one another from an open position, wherein jaw members 21 and 22 are disposed in spaced-apart relation relative to one another, to a closed position, wherein jaw members 21 and 22 cooperate to grasp tissue therebetween.

A ratchet 230 may be included for selectively locking jaw members 21 and 22 of forceps 200 relative to one another at various different positions. It is envisioned that ratchet 230 may include graduations or other visual markings that enable the user to easily and quickly ascertain and control the amount of closure force desired between the jaw members 21 and 22.

With continued reference to FIG. 2, one of the shafts may be adapted to receive a surgical cable configured to connect forceps 200 to a power source (not shown). Alternatively, forceps 200 may be configured as a battery powered instrument having an internal or integrated power source (not shown). The power source (not shown), as will be described in greater detail below, provides power to end effector assembly 20 such that at least one of the electrically-conductive tissue treating surfaces 23, 24 of jaw members 21, 22, respectively, of end effector assembly 20 may be energized to treat tissue grasped therebetween.

Similar to forceps 100 (FIG. 1), forceps 200 may further include a knife assembly (not shown) disposed within either of shafts 212a, 212b and a knife channel 615, 625 (FIG. 6) defined within one or both jaw members 21, 22 to permit reciprocation of a knife blade (not shown) therethrough.

Turning now to FIG. 3, reposable forceps 300 may be configured as an open forceps, e.g., similar to forceps 200 (FIG. 2), an endoscopic forceps, e.g., similar to forceps 100 (FIG. 1), or in any other suitable configuration. Reposable forceps 300 includes an end effector assembly 30 similar to end effector assemblies 10, 20 (FIGS. 1, 2, respectively), except that jaw members 31, 32 each include a fixed jaw frame 31a, 32a and a removable jaw body 31b, 32b, respectively. Jaw bodies 31b, 32b are removably engagable with respective jaw frames 31a, 32a and each includes an electrically-conductive tissue treating surface 33, 34, respectively. Either or both of tissue treating surfaces 33, 34 are adapted to receive energy for treating tissue grasped between jaw members 31, 32.

Referring now to FIG. 4, tissue clip 400 is an integrated or stand-alone end effector assembly including first and second jaw members 41, 42, respectively, coupled to one another by a flexible joint 43, although jaw members 41, 42 may alternatively be coupled to one another by a hinge, pivot, or any other suitable mechanism. Flexible joint 43 permits jaw members 41, 42 to move relative to one another between spaced-apart and approximated positions for grasping tissue therebetween. Jaw members 41, 42 of tissue clip 400 each further include an electrically-conductive tissue treating surface 44, 45, respectively. A power source, e.g., battery 46, energy generating component 47, and control electronics 48 are disposed within either or both of jaw members 41, 42 for providing power to tissue clip 400, converting the power into energy for treating tissue, and controlling the supply of energy delivered to electrically conductive tissue treating surfaces 44, 45 of jaw members 41, 42, respectively, to treat, e.g., seal, tissue grasped between jaw members 41, 42. A latch mechanism 49 including first and second latch components 49a, 49b disposed on first and second jaw members 41, 42, respectively, may also be provided for selectively locking jaw members 41 and 42 relative to one another in various different positions.

Figure 5:
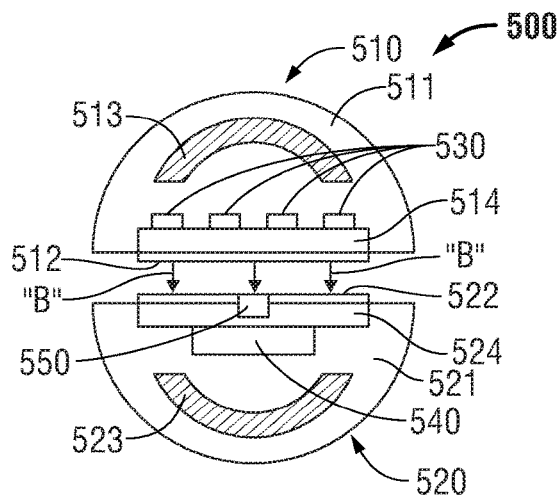
FIG. 5 is a transverse, cross-sectional view of an end effector assembly configured for use with any of the instruments of FIGS. 1-4.
Figure 6:
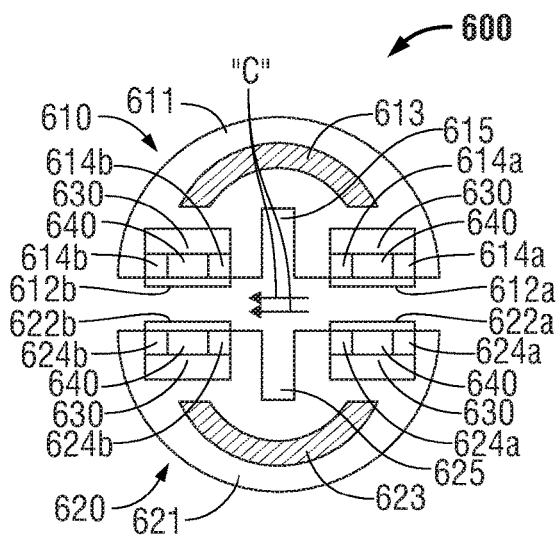
FIG. 6 is a transverse, cross-sectional view of another end effector assembly configured for use with any of the instruments of FIGS. 1-4.
Figure 7:
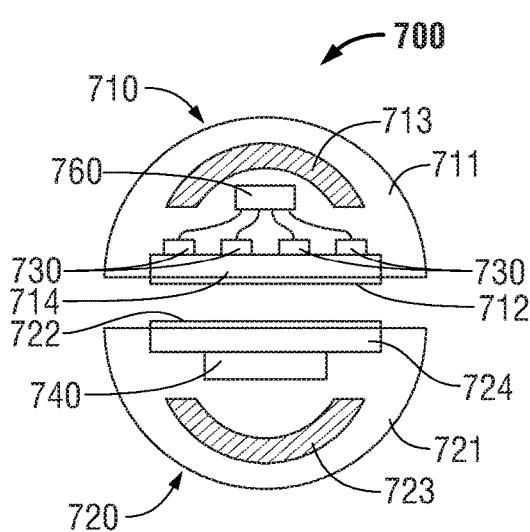
FIG. 7 is a transverse, cross-sectional view of another end effector assembly configured for use with any of the instruments of FIGS. 1-4.

Turning now to FIGS. 5-7, various embodiments of end effector assemblies 500, 600, 700 configured for use with forceps 100 (FIG. 1), forceps 200 (FIG. 2), forceps 300 (FIG. 3), and/or tissue clip 400 (FIG. 4) are shown. Although shown as separate embodiments, any or of all of the features of end effector assemblies 500, 600, 700, to the extent that they are consistent, may similarly be used in conjunction with any other end effector assembly 500, 600, 700. Further, although described below with respect to RF energy, end effector assemblies 500, 600, 700 may alternatively be configured for use with light, microwave, ultrasonic, resistive, or other suitable forms of energy for treating tissue.

Continuing with general reference to FIGS. 5-7, each end effector assembly 500, 600, 700 incorporates or is coupled to a power system, energy generating system, and/or control system in thermal communication with the tissue treating surface thereof to facilitate energy-based tissue treatment, e.g., tissue sealing. More specifically, as will be described in greater detail below, by coupling the power system, energy generation system, and/or control system to the tissue treating surfaces of the jaw members, the waste heat produced as a by-product of these systems can be used to facilitate the heating of tissue and/or to facilitate uniform tissue heating. This configuration not only facilitates effective tissue treatment, but also eliminates the need for heat dissipation systems, thereby reducing complexity; and utilizes waste heat, thereby increasing efficiency and/or reducing the overall power required to treat tissue.

With reference to FIG. 5, end effector assembly 500 includes first and second jaw members 510, 520, respectively, each including a jaw housing 511, 521 and an electrically and thermally-conductive tissue treating surface 512, 522, respectively. Jaw housings 511, 521 are formed from insulative materials and are supported on a jaw frame 513, 523, respectively. Jaw frames 513, 523 are coupled to one another, e.g., via a pivot (not shown), to permit movement of jaw members 510, 520 relative to one another between a spaced-apart position and an approximated position for grasping tissue therebetween. Tissue treating surfaces 512, 522 are disposed on jaw housings 511, 521, respectively, and are configured to grasp tissue therebetween upon movement of jaw members 510, 520 to the approximated position. Upon energization, tissue treating surfaces 512, 522 of jaw members 510, 520, respectively, are configured to conduct energy therebetween and through tissue grasped between jaw members 510, 520 to treat tissue. More specifically, tissue treating surface 512 is charged to a first electrical potential and tissue treating surface 522 is charged to a second, different electrical potential thereby creating an electrical potential gradient between tissue treating surfaces 512, 522 of jaw members 510, 520, respectively, such that electrical energy may be conducted therebetween and through tissue grasped therebetween to treat tissue. As shown by arrows "B," energy is conducted through tissue in a generally perpendicular direction relative to tissue grasped between jaw members 510, 520, although other configurations are also contemplated. Tissue treating surfaces 512, 522 are further configured to conduct thermal energy to tissue grasped therebetween, as will be described in greater detail below.

Continuing with reference to FIG. 5, one or both jaw members 510, 520 further include a substrate 514, 524, respectively, disposed therein and positioned adjacent to and in thermal communication with the respective tissue treating surface 512, 522 thereof. Substrates 514, 524 of jaw members 510, 520, respectively, incorporate or mount the energy generation system and/or control system of end effector assembly 500 therein, as will be described in greater detail below. Insulative jaw housings 511, 521 encapsulate respective substrates 514, 524 such that substrates 514, 524 are thermally coupled to tissue treating surfaces 512, 522, respectively, but are otherwise surrounded by a thermally insulating material. One of jaw members 510, 520 may further include a battery (not shown) disposed therein for providing power to end effector assembly 500, e.g., the energy generation system and/or control system thereof, or, alternatively, end effector assembly 500 may be powered by an external or remote power source (not shown), similarly as described above with respect to forceps 100 (FIG. 1).

Each substrate 514, 524 may be formed from a printed circuit board (PCB), a ceramic substrate, or other suitable material, composite, or assembly that incorporates or mounts the energy generation system and/or control system of end effector assembly 500 thereon and is configured to permit the conduction or transfer of heat from the energy generation system and/or control system thereof to the respective tissue treating surface 512, 522 of jaw members 510, 520, e.g., substrates 514, 524 may be formed from thermally-conductive materials in contact with tissue treating surfaces 512, 522 or may otherwise be configured to facilitate thermal conduction between the energy generation system and/or control system and the respective tissue treating surfaces 512, 522 (e.g., via wires, traces, etc.). The energy generation system and/or control system may be formed on substrates 514, 524 as integrated circuits (ICs) on a PCB, multi-chip modules (MCMs) packaged in a ceramic (or other suitable) substrate, System-in-Package (SiP) modules, or other suitable electronics for generating the energy, e.g., RF energy, to be delivered to tissue and/or for controlling the delivery of the energy to tissue.

Substrate 514 of jaw member 510 may include one or more RF-energy generating units 530 (or, alternatively, light energy generating units, microwave energy generating units, etc., depending on the type of energy to be provided) that are coupled to tissue treating surface 512, e.g., via wires or traces (not explicitly shown), for providing electrical, e.g., RF, energy to tissue treating surface 512 for conducting electrical energy between tissue treating surfaces 512, 522 to treat tissue grasped therebetween. For example, substrate 514 may include a ceramic substrate in thermal communication (e.g., in contact) with electrically and thermally-conductive tissue treating surface 512 and incorporating one or more RF-energy generating IC's 530 therein, thus forming an MCM. Other configurations, such as those mentioned above, are also contemplated. In addition to generating RF energy for conduction through tissue to heat and, thus, treat tissue, the RF-energy generating units 530 and the components thereof, e.g., transistors, resistors, capacitors, inductors, etc., also produce waste heat as a by-product of RF-energy generation. This waste heat produced by the RF-energy generating units 530 is conducted through the ceramic substrate 514 to heat tissue treating surface 512 (as a result of the thermal communication therebetween) and, ultimately, to heat, tissue grasped between jaw members 510, 520. That is, rather than requiring the dissipation of waste heat from the energy generating system, e.g., RF-energy generating units 530, the waste heat is used to facilitate the heating of tissue grasped between jaw members 510, 520 (in addition to tissue heating effected via the conduction of RF energy therethrough), thereby increasing the efficiency of the system and requiring relatively less power to sufficiently treat, e.g., seal, tissue. This configuration also facilitates more uniform heating of tissue by counteracting any heat sinking effects of jaw members 510, 520.

Substrate 524 of jaw member 520, on the other hand, may include a control unit 540 for controlling the supply of electrical energy to tissue grasped between jaw members 510, 520, although either or both jaw members 510, 520 may include the energy-generating and/or control components of end effector assembly 500. Control unit 540 may include logic or processing circuitry, e.g., microprocessors, field-programmable gate arrays (FPGAs), discrete logic circuits, etc.; timing circuitry; sensing elements, e.g., temperature sensors, pressure sensors, tissue property sensors, etc.; and/or other control circuitry for controlling the supply of RF energy to tissue treating surfaces 512, 522 of jaw members 510, 520, respectively. Control unit 540, for example, may include one or more IC's incorporated into a ceramic substrate 524, or any other suitable configuration, such as those mentioned above. Similarly as described above with respect to jaw member 510, control unit 540 and the components thereof, e.g., transistors, resistors, capacitors, inductors, etc., in addition to performing control functions, also produce waste heat as a by-product of the operation thereof. This waste heat is conducted to tissue treating surface 522 (due to the thermal communication between substrate 524 and tissue treating surface 522) and, ultimately, to tissue grasped between jaw members 510, 520 to facilitate heating of tissue grasped therebetween. As such, more uniform tissue heating is achieved, the efficiency of the system is increased, and/or relatively less power is required to sufficiently treat, e.g., seal, tissue. The features and/or functions of control unit 540 will be described in greater detail below.

With continued reference to FIG. 5, and with additional reference to FIG. 1, the use and operation of end effector assembly 500 in conjunction with forceps 100 is described. Although the use and operation of end effector assembly 500 is described with respect to forceps 100, end effector assembly 500 may be similarly configured for use with forceps 200, forceps 300, or tissue clip 400 (FIGS. 2, 3, and 4, respectively).

Initially, with jaw members 510, 520 disposed in the spaced-apart position, end effector assembly 500 is maneuvered into position such that tissue to be grasped and treated, e.g., sealed, is disposed between jaw members 510, 520. Next, movable handle 140 is depressed, or pulled proximally relative to fixed handle 150 such that jaw member 510 is pivoted relative to jaw member 520 from the spaced-apart position to the approximated position to grasp tissue therebetween. More specifically, upon actuation of movable handle 150, a drive assembly (not shown) is activated such that a drive bar (not shown) is translated proximally through shaft 112, causing jaw member 510 to pivot relative to jaw member 520 from the spaced-apart position to the approximated position. Once disposed in the approximated position grasping tissue between tissue treating surfaces 512, 522 of jaw members 510, 520, respectively, power may be supplied to end effector assembly 500, e.g., via manual activation of switch 190, automatically via activation of control unit 540, or upon satisfaction of some condition, as will be described below. As mentioned above, an external power source (not shown) may be coupled to forceps 100 for providing electrical power to end effector assembly 500 or, alternatively, housing 120 of forceps 100 may include a portable battery (not shown) disposed therein. In either embodiment, the power source (not shown) need only be configured to provide standard electrical power to end effector assembly 500, as the energy generating system, e.g., RF-energy generating units 530, and control system, e.g., control unit 540, are fully contained within end effector assembly 500.

Upon activation, e.g., upon initiation of the sealing cycle, electrical power is supplied to end effector assembly 500, as mentioned above, and, more particularly, is transmitted to RF-energy generating units 530 which, in turn, convert the electrical power into RF energy, e.g., in the frequency range of about 100 KHz to about 10 MHz. The RF energy is then transmitted to tissue treating surface 512 of jaw member 510 for conduction between tissue treating surface 512 of jaw member 510 and tissue treating surface 522 of jaw member 520 and through tissue grasped therebetween to seal, or otherwise treat tissue. With respect to tissue sealing in particular, the compression of tissue between jaw members 510, 520 brings tissue walls together and the application of RF energy to tissue heats tissue to the temperature of denaturizing and mixing of collagen and elastin to form an effective tissue seal upon the cooling down and solidification of the melted collagen and elastin. As mentioned above, the heating of tissue is furthered by the application of the waste heat produced by RF-energy generating units 530 to tissue. Thus, RF-energy generating units 530 produce the RF energy that is conducted through tissue to heat tissue (via Joule heating) and also produce waste heat that is used to conductively heat tissue, thereby supplementing the heating of tissue, increasing efficiency, reducing power requirements, and facilitating uniform tissue heating.

Heating of tissue to the target temperature for forming an effective tissue seal is dependent on a number of factors including the compressive force applied to tissue by jaw members 510, 520, the size and/or composition of tissue, the amount of energy supplied to tissue, and other factors. Control unit 540 of end effector assembly 500, as mentioned above, is used to control the supply of energy to tissue treating surfaces 512, 522 of jaw members 510, 520, respectively, e.g., in accordance with one or more of these factors, such that formation of an effective tissue seal (or otherwise effectively treating tissue) can be achieved. That is, control unit 540 and RF-energy generating units 530 cooperate to start, regulate, and end the sealing cycle to facilitate formation of an effective tissue seal. Control unit 540 may be configured to individually and/or collectively control RF-energy generating units 530.

Control unit 540 may further include or may be coupled to one or more sensors 550 disposed on or along jaw member 520 (and/or jaw member 510) that are configured to automatically sense various properties of the tissue including, but not limited to: tissue impedance, tissue type, reflectance, transmittance, tissue compliance, tissue temperature, temperature of jaw members 510, 520, water content in tissue, opening angle of jaw members 510, 520, water motility in tissue, energy delivery treating pressure, and/or jaw member closure pressure. One or more sensors 550 may additionally or alternatively be configured to sense output voltage, current, impedance, and/or power from RF-energy generating units 530. As will become more apparent in view of the following, sensors 550 provide feedback to control unit 540, thus allowing control unit 540 to control RF-energy generating units 530 to achieve the desired tissue treatment With regard to initiation of the sealing cycle, as mentioned above, RF-energy generating units 530, when activated, produce and supply energy to tissue treating surfaces 512, 522 of jaw members 510, 520, respectively, for sealing tissue grasped therebetween. Control unit 540 may activate RF-energy generating units 530 to initiate the sealing cycle manually, e.g., upon activation of switch 190, upon reaching a particular mechanical condition, e.g., upon closure of jaw members 510, 520 to a pre-determined gap distance (as sensed by one or more of sensors 550) or upon achieving a pre-determined closure pressure applied to tissue grasped between jaw members 510, 520 (as sensed by one or more of sensors 550), or in any other suitable fashion.

With regard to regulation and ending (completion) of the sealing cycle, the detected tissue properties and/or other properties detected by sensor(s) 550 may be configured to provide feedback to control unit 540 which, in turn, controls the output of RF-energy generating units 530 via an open loop or closed loop scheme. Alternatively or additionally, control unit 540 may be configured to control the sealing cycle according to a predetermined algorithm, e.g., via a timing circuit, a pre-defined voltage profile or voltage-controlled algorithm, or via temperature control, e.g., the temperature of tissue may be monitored such that RF-energy generating units 530 are turned off upon reaching a pre-determined temperature, upon achieving a pre-determined temperature for a pre-determined length of time, and/or upon reaching a particular rate-of-change of tissue temperature. Other algorithms or functions for controlling the sealing cycle may include: ending the cycle after sensing a peak and subsequent flattening out of delivered power, ending the seal cycle upon sensing a decrease in tissue thickness, and ending the seal cycle upon sensing and abrupt change in resistance, impedance, and/or capacitance. Similarly as mentioned above with respect to RF-energy generating units 530, during the sealing cycle, heating of tissue is supplemented by the conduction of the waste heat produced by control unit 540 to tissue. That is, control unit 540 not only controls the seal cycle, but also facilitates formation of a uniform tissue seal (or otherwise effective treatment of tissue) with greater efficiency and reduced power requirements.

At the completion of tissue sealing, or other tissue treatment, a knife (not shown) may be advanced from shaft 112 of forceps 100 between jaw members 510, 520 to cut previously-sealed tissue grasped therebetween, e.g., upon actuation of trigger 182 of trigger assembly 180. Thereafter, or in embodiments where a knife assembly (not shown) is not provided, jaw members 510, 520 may be returned to the spaced-apart position to release the sealed and/or divided tissue, e.g., via moving movable handle 140 back to the initial position.

Referring now to FIG. 6, another embodiment of an end effector assembly 600 configured for use with forceps 100 (FIG. 1), forceps 200 (FIG. 2), forceps 300 (FIG. 3), and/or tissue clip 400 (FIG. 4) is shown. End effector assembly 600 is similar to end effector assembly 500 (FIG. 5) and, thus, only the differences between end effector assembly 600 and end effector assembly 500 (FIG. 5) will be described in detail hereinbelow, while similarities will only be summarily described or omitted entirely to avoid unnecessary repetition.

End effector assembly 600 includes first and second jaw members 610, 620, respectively, each including a jaw housing 611, 621 supported on a jaw frame 613, 623 and a pair of tissue treating surfaces 612a, 612b an 622a, 622b disposed on respective jaw housings 611, 621. One or both of jaw members 610, 620 is movable relative to the other between a spaced-apart position and an approximated position for grasping tissue therebetween. The tissue treating surfaces 612a, 612b and 622a, 622b of each jaw member 610, 620 are disposed on either side of a knife channel 615, 625 extending longitudinally through the respective jaw member 610, 620 and are adapted to conduct energy therebetween and through tissue grasped between jaw members 610, 620 to thermally treat, e.g., seal, tissue. More specifically, tissue treating surfaces 612a, 612b and 622a, 622b are arranged transversely such that tissue treating surfaces 612a, 622a may be charged to a first electrical potential while tissue treating surfaces 612b, 622b are charged to a second, different electrical potential thereby creating an electrical potential gradient between tissue treating surfaces 612a, 622a and tissue treating surfaces 612b, 622b to conduct energy therebetween and through tissue grasped between jaw members 610, 620 in a generally parallel direction relative to tissue, as indicated by arrows "C," to heat and treat tissue. Alternatively, tissue treating surfaces 612a, 612b of jaw member 610 may be charged to a first potential and tissue treating surfaces 622a, 622b of jaw member 620 may be charged to a second potential, similarly as described above with respect to end effector assembly 500 (FIG. 5).

Continuing with reference to FIG. 6, each jaw member 610, 620 includes a pair of substrates 614a, 614b and 624a, 624b, respectively, disposed therein and positioned adjacent to one of the respective tissue treating surfaces 612a, 612b and 622a, 622b. Each substrate 614a, 614b, 624a, 624b incorporates or mounts an RF-energy generating unit 630 and a control unit 640 for supplying and controlling the supply of RF-energy to tissue treating surfaces 612a, 612b, 622a, 622b, respectively. Sensors (not explicitly shown) may also be provided for use in conjunction with one or more of substrates 614a, 614b, 624a, 624b. The RF-energy generating unit 630 and control unit 640 corresponding to each of tissue treating surfaces 612a, 612b, 622a, 622b may be independently or collectively operated. One of jaw members 610, 620 may further include a battery (not shown) disposed therein for providing power to end effector assembly 600, e.g., the energy generation systems and/or control systems thereof, or, alternatively, end effector assembly 600 may be powered by an external or remote power source (not shown).

The transverse configuration of tissue treating surfaces 612a, 612b, 622a, 622b facilitates tissue treatment, e.g., tissue sealing, with reduced power requirements and reduced thermal spread. Tissue treatment is further facilitated and more efficiently effected by the use of waste heat produced by the RF-energy generating unit 630 and control unit 640. In particular, the transverse configuration of tissue treating surfaces 612a, 612b, 622a, 622b, in use, heats tissue between the pairs of tissue treating surfaces 612a, 612b and 622a, 622b greater than tissue adjacent tissue treating surfaces 612a, 612b, 622a, 622b. However, the use of the waste heat produced by RF-energy generating units 630 and control units 640 is conducted to the tissue treating surfaces 612a, 612b, 622a, 622b, thereof to conductively heat tissue adjacent tissue treating surfaces 612a, 612b, 622a, 622b, thus counteracting the non-uniform heating effects of the transverse electrodes and allowing for more uniform heating of tissue. End effector assembly 600 may otherwise be similar in configuration and operation, and may include any or all of the features of end effector assembly 500 (FIG. 5), described above, and vice versa.

Turning now to FIG. 7, another embodiment of an end effector assembly 700 configured for use with forceps 100 (FIG. 1), forceps 200 (FIG. 2), forceps 300 (FIG. 3), and/or tissue clip 400 (FIG. 4) is shown. End effector assembly 700 is similar to end effector assembly 500 (FIG. 5) and, thus, only the differences between end effector assembly 700 and end effector assembly 500 (FIG. 5) will be described in detail hereinbelow, while similarities will only be summarily described or omitted entirely to avoid unnecessary repetition.

With continued reference to FIG. 7, end effector assembly 700 includes first and second jaw members 710, 720, respectively, each including a jaw housing 711, 721 supported on a jaw frame 713, 723 and an electrically-conductive tissue treating surface 712, 722, respectively, disposed on jaw housings 711, 721, respectively. One or both jaw members 710, 720 further include a substrate 714, 724, respectively, disposed therein and positioned adjacent to and in thermal communication with the respective tissue treating surface 712, 722 thereof. Substrates 714, 724 of jaw members 710, 720, respectively, incorporate or mount the RF-energy generating units 730 and control unit 740, respectively, of end effector assembly 700 therein. One of the jaw members, e.g., jaw member 710, further includes a power source, or battery 760 disposed therein for providing power to end effector assembly 700, e.g., the energy generation system and/or control system thereof. Battery 760 may be a rechargeable battery or a single-use battery and may also be thermally coupled to tissue treating surface 712, e.g., via substrate 714, such that the waste heat produced by battery 760 may also be used to facilitate formation of an efficient, effective tissue seal.

End effector assembly 700 (or end effector assemblies 500, 600, in embodiments including an internal power source similar to battery 760) is particularly suitable for use in conjunction with a tissue clip, e.g., tissue clip 400 (FIG. 4), in that end effector assembly 700 incorporates the power, energy-generation, and control systems therein and, as a result, no external electronics are required. Thus, in use, with additional reference to FIG. 4, tissue clip 400 may be placed in the body of a patient approximately near tissue to be treated. Jaw members 710, 720 may then be approximated relative to one another to grasp tissue therebetween and may be retained in the approximated position using latch assembly 49. RF-energy generating units 730, control unit 740, and battery 760 may then be operated to treat, e.g., seal, tissue grasped between jaw members 710, 720, similarly as described above. More specifically, control unit 740 may automatically initiate, regulate and/or end (complete) the sealing cycle, as described above, such that tissue clip 400 may be clipped or latched about tissue and left in position to form a tissue seal, without the need to monitor tissue clip 400. Alternatively, control unit 740 of tissue clip 400 may be controlled remotely, e.g., wirelessly, via a remote control, user interface, or other suitable device. Use of end effector assembly 700, however, is not limited to tissue clip 400, as end effector assembly 700 may also be configured for use with any other suitable surgical instrument. End effector assembly 700 may otherwise be similar in configuration and operation, and may include any of the features of end effector assembly 500 (FIG. 5) or end effector assembly 600 (FIG. 6), described above, and vice versa.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A medical device, comprising:
   first and second electrically and thermally conductive tissue treating surfaces;
   an electrical conductor disposed in electrical communication with the first tissue treating surface and configured to conduct RF energy to the first tissue treating surface for conducting RF energy through tissue disposed between the first and second tissue treating surfaces for heating tissue via Joule heating to treat tissue; and
   an electrically insulative thermal conductor disposed in thermal communication with the first tissue treating surface and configured to conduct heat to the first tissue treating surface for heating tissue adjacent the first tissue treating surface via conductive heating to facilitate treating tissue,
   wherein the electrically insulative thermal conductor is coupled to heat-generating electronics for conducting the heat from the heat-generating electronics to the first tissue treating surface, and wherein the heat-generating electronics include at least one of a control unit or a power source.

2. The medical device according to claim 1, wherein the electrical conductor is coupled to a source of RF energy for conducting the RF energy from the source of RF energy to the first tissue treating surface.

3. The medical device according to claim 1, further comprising first and second jaw members including the first and second tissue treating surfaces, respectively, disposed thereon, at least one of the first or second jaw members movable relative to the other to grasp tissue between the first and second tissue treating surfaces.

4. The medical device according to claim 3, wherein the heat-generating electronics are disposed within the first jaw member.

5. The medical device according to claim 3, further comprising an RF energy generating unit disposed within the first jaw member, wherein the electrical conductor is coupled to the RF energy generating unit for conducting the RF energy from the RF energy generating unit to the first tissue treating surface.

6. A medical device, comprising:
   first and second electrically and thermally conductive tissue treating surfaces; and
   an electrical conductor electrically coupled to the first tissue treating surface, the electrical conductor configured to conduct RF energy to the first tissue treating surface for conducting RF energy through tissue disposed between the first and second tissue treating surfaces for heating tissue via Joule heating to treat tissue;
   heat-generating electronics including at least one of a control unit or a power source; and
   an electrically insulative thermal conductor thermally coupling the heat-generating electronics and the first tissue treating surface, the electrically insulative thermal conductor configured to conduct heat produced by the heat-generating electronics to the first tissue treating surface for heating tissue adjacent the first tissue treating surface via conductive heating to facilitate treating tissue.

7. The medical device according to claim 6, wherein the electrical conductor is coupled to a source of RF energy for conducting the RF energy from the source of RF energy to the first tissue treating surface.

8. The medical device according to claim 6, further comprising first and second jaw members including the first and second tissue treating surfaces, respectively, disposed thereon, at least one of the first or second jaw members movable relative to the other to grasp tissue between the first and second tissue treating surfaces.

9. The medical device according to claim 8, wherein the heat-generating electronics are disposed within the first jaw member.

10. The medical device according to claim 8, further comprising an RF energy generating unit disposed within the first jaw member, wherein the electrical conductor is coupled to the RF energy generating unit for conducting the RF energy from the RF energy generating unit to the first tissue treating surface.

11. A method of treating tissue, comprising:
   conducting RF energy, via an electrical conductor, to a first electrically and thermally conductive tissue treating surface such that the RF energy is conducted through tissue disposed between the first tissue treating surface and a second electrically and thermally conductive tissue treating surface to heat tissue via Joule heating to treat tissue;
   conducting heat, via an electrically insulative thermal conductor, to the first tissue treating surface such that the first tissue treating surface is heated to heat tissue adjacent the first tissue treating surface via conductive heating to facilitate treating tissue; and
   controlling the conduction of RF energy using a control unit, wherein conducting heat, via the electrically insulative thermal conductor, to the first tissue treating surface includes conducting heat from the control unit.

12. The method according to claim 11, wherein conducting heat, via the electrically insulative thermal conductor, to the first tissue treating surface further includes conducting heat from an RF energy generating unit.

13. The method according to claim 11, further comprising powering the surgical instrument from a power source.

14. The method according to claim 13, wherein conducting heat, via the electrically insulative thermal conductor, to the first tissue treating surface further includes conducting heat from the power source.

* * * * *